(12) United States Patent
Harris

(10) Patent No.: US 7,229,800 B2
(45) Date of Patent: Jun. 12, 2007

(54) NEISSERIA GONORRHOEAE ASSAY

(75) Inventor: James M. Harris, Owings Mills, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 26 days.

(21) Appl. No.: 10/825,908

(22) Filed: Apr. 16, 2004

(65) Prior Publication Data

US 2005/0233331 A1    Oct. 20, 2005

(51) Int. Cl.
- C12P 19/34    (2006.01)
- C12Q 1/68     (2006.01)
- C07H 21/02    (2006.01)
- C07H 21/04    (2006.01)

(52) U.S. Cl. .................. 435/91.2; 435/6; 536/23.1; 536/24.3

(58) Field of Classification Search ............ None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,755,458 A | 7/1988 | Rabbani et al. |
| 4,800,159 A | 1/1989 | Mullis et al. |
| 4,900,659 A | 2/1990 | Lo et al. |
| 4,965,188 A | 10/1990 | Mullis et al. |
| 5,102,784 A | 4/1992 | George |
| 5,108,895 A | 4/1992 | Woods et al. |
| 5,130,238 A | 7/1992 | Malek et al. |
| 5,173,401 A | 12/1992 | Wolff et al. |
| 5,256,536 A | 10/1993 | Miyada et al. |
| 5,270,184 A | 12/1993 | Walker et al. |
| 5,378,606 A | 1/1995 | Stern et al. |
| 5,389,515 A | 2/1995 | Chmelo et al. |
| 5,427,930 A | 6/1995 | Birkenmeyer et al. |
| 5,432,271 A | 7/1995 | Barns et al. |
| 5,453,355 A | 9/1995 | Birkenmeyer et al. |
| 5,455,166 A | 10/1995 | Walker |
| 5,470,723 A | 11/1995 | Walker et al. |
| 5,536,638 A | 7/1996 | Rossau et al. |
| 5,550,040 A | 8/1996 | Purohit et al. |
| 5,595,874 A | 1/1997 | Hogan et al. |
| 5,648,211 A | 7/1997 | Fraiser et al. |
| 5,712,124 A | 1/1998 | Walker |
| 5,744,311 A | 4/1998 | Fraiser et al. |
| 5,814,490 A | 9/1998 | Spears |
| 5,928,869 A | 7/1999 | Nadeau et al. |
| 5,958,700 A | 9/1999 | Nadeau et al. |
| 5,962,273 A | 10/1999 | Durmowicz et al. |
| 5,976,805 A | 11/1999 | You |
| 6,316,200 B1 | 11/2001 | Nadeau et al. |
| 6,379,888 B1 | 4/2002 | Nadeau |

FOREIGN PATENT DOCUMENTS

| | | |
|---|---|---|
| EP | 0 353 985 | 2/1990 |
| EP | 0 497 272 | 8/1992 |
| EP | 0 624 643 | 11/1994 |
| EP | 0 678 582 | 10/1995 |
| EP | 0 684 315 | 11/1995 |
| EP | 0 317 077 | 1/1996 |
| EP | 0 747 489 | 12/1996 |
| EP | 0 823 485 | 2/1998 |
| WO | WO-89/03891 | 5/1989 |
| WO | WO-91/03573 | 8/1990 |
| WO | WO-90/10064 | 9/1990 |
| WO | WO-94/06817 | 3/1994 |

OTHER PUBLICATIONS

Barany, Genetic Disease Detection and DNA Amplification Using Cloned Thermostable Ligase, *Proc. Natl. Acad. Sci. USA*, 88(1): 189-93 (1991).

Barringer et al., Gene, 89:117-122 (1990).

Buimer et al., Detection of *Chlamydia trachomatis* and *Neisseria gonnorrhoeae* by Ligase Chain Reaction-Based Assays with Clinical Specimens from Various Sites: Implications for Diagnostic Testing and Screening, *J. Clinical Microbiology*, 34(10):2395-2400 (Oct. 1996).

Chan et al., Performance Characteristics of the Becton Dickinson Probe Tec System for Direct Detection of *Chlamydia trachomatis* and *Neisseria gonorrhoeae* in male and female urine specimens in comparison with the Roche Cobas System, *Arch. Pathol. Lab. Med.*, 124(11):1649-52 (2000).

Crotchfelt et al., Detection of *Neiseria gonorrhoeae* and *Chlamydia trachomatis* in Genitourinary Specimens from Men and Women by a Coamplification PCR Assay, *J. of Clinical Microbiology*, 35(6): 1536-1540 (Jun. 1997).

Donegan, James J. Isolation of a species-specific DNA probe for *Neisseria gonorrhoeae* using a novel technique particularly suitable for use with closely related species displaying high levels of DNA homology, *Moll. Cell. Prob.*, 3:13-26 (1989).

Guatelli et al., Isothermal, in vitro Amplification of Nucleic Acids by a Multienzyme Reaction Modeled After Retroviral Replication, *Proc. Natl. Acad. Sci. USA*, 87(5): 1874-8 (1990).

Herrmann et al., Detection of *Neisseria gonorrhoeae* from Air-Dried Genital Samples by Single-Tube Nested PCR, *J. of Clinical Microbiology*, 34(10):2548-2551 (Oct. 1996).

(Continued)

Primary Examiner—Jeffrey Fredman
Assistant Examiner—Suchira Pande
(74) Attorney, Agent, or Firm—Allan M. Kiang

(57) ABSTRACT

The present invention relates to nucleic acid amplification assays for the detection of nucleic acid sequences of *Neisseria gonorrhoeae*. The present invention provides oligonucleotides that are complementary or that anneal to nucleic acid sequences of *Neisseria gonorrhoeae*. The present invention also provides internal amplification controls (IACs) that can be used in nucleic acid amplification reactions.

17 Claims, 1 Drawing Sheet

OTHER PUBLICATIONS

Iwen et al., Evaluation of Nucleic Acid-Based Test (PACE 2C) for Simultaneous Detection of *Chylamydia trachomatis* and *Neisseria gonorrhoeae* in Endocervical Specimens, *J. of Clinical Microbiology*, 33(10):2587-2591 (Oct. 1995).

Jephcott, A.E., *Microbiological Diagnosis of Gonorrhoea*, *Genitourin Med.*, 73:245-252 (1997).

Kwoh et al., Transcription-based Amplification System and Detection of Amplified Human Immunodeficiency Virus Type 1 with a bead-Based Sandwich Hybridization Format, *Proc. Natl. Acad. Sci. USA*, 86(4): 1173-7 (1989).

Little et al., *Clinical Chemistry*, 45(6): 777-784 (1999).

Lizardi et al., *Bio Technology*, 6: 1197-1202 (1988).

Lizardi et al., Mutation Detection and Single-Molecule Counting Using Isothermal Rolling-Circle Amplification, *Nat. Genet.* 19(3): 225-32 (1998).

Saiki et al., *Science*, 230: 1350-1354 (1985).

Schoone et al., Comparison of Dot Blot with in-situ Hybridization for the Detection of *Neisseria gonorrhoeae* in the Urethral Exudate, *J. of Applied Bateriology*, 66:401-405 (1989).

Stary et al., Comparison of Ligase Chain Reaction and Culture of Detection of *Neisseria gonnorrhoeae* in Genital and Extragenital Speecimens, *J. of Clinical Microbiology*, 35(1):239-242 (Jan. 1997).

Totten et al., DNA Hybridization Technique for the Detection of *Neisseria gonorrhoeae* in Men with Urethritis, *The Journal of Infectious Diseases*, 148(3):462-471 (Sep. 1983).

Walker et al., Isothermal in-vitro Amplification of DNA by a Restriction Enzyme/DNA Polymerase System, *PNAS*, 89:392-396 (1992).

Walker et al., Strand Displacement Amplification-an isothermal, in-vitro DNA Amplification Technique, *Nucl. Acids Res.*, 20:1691-1696 (1992).

Watson et al., Recombinant DNA, *Scientific American Books*, New York, pp. 67-69, 1992.

Wu et al., *Genomics*, 4: 560-569 (1989).

Figure 1. The Positions of the Annealing Regions of Oligonucleotides that Form the GCINT3 SDA Assay
A. The GCINT3 Assay Region
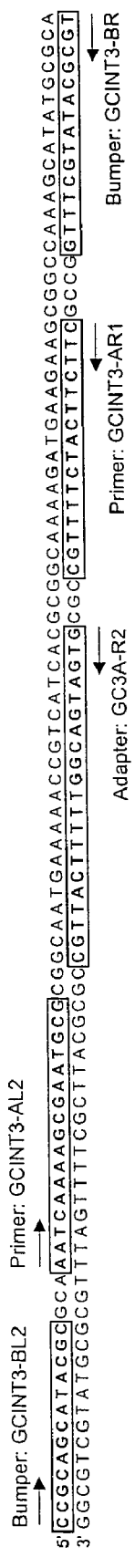
B. The GCl3-IAC4 Region:
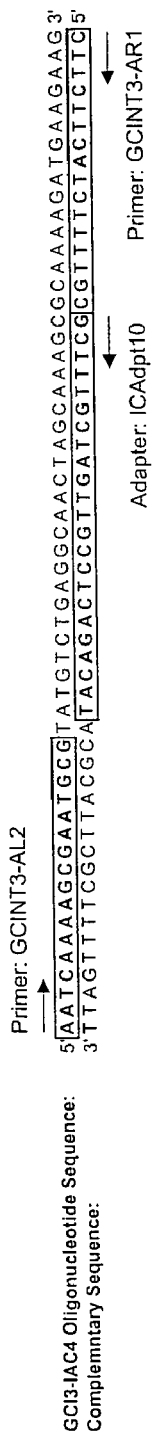

SEQUENCE LISTING

<160> NUMBER OF SEQ ID NOS: 23

<210> SEQ ID NO 1
<211> LENGTH: 41
<212> TYPE: DNA
<213> ORGANISM: Artificial Sequence
<220> FEATURE:
<223> OTHER INFORMATION: Amplification Primer

<400> SEQUENCE: 1
cgtctccagt ccagacttct cgggaatcaa aagcgaatgc g          41

<210> SEQ ID NO 2
<211> LENGTH: 41
<212> TYPE: DNA
<213> ORGANISM: Artificial Sequence
<220> FEATURE:
<223> OTHER INFORMATION: Amplification Primer

<400> SEQUENCE: 2
actacgtcga atgcatgtct cgggacttct tcatcttttg c          41

<210> SEQ ID NO 3
<211> LENGTH: 13

```
<212> TYPE: DNA
<213> ORGANISM: Artificial Sequence
<220> FEATURE:
<223> OTHER INFORMATION: Bumper Primer

<400> SEQUENCE: 3
ccgcagcata cgc                                                     13

<210> SEQ ID NO 4
<211> LENGTH: 15
<212> TYPE: DNA
<213> ORGANISM: Artificial Sequence
<220> FEATURE:
<223> OTHER INFORMATION: Bumper Primer

<400> SEQUENCE: 4
tgcgcatatg ctttg                                                   15

<210> SEQ ID NO 5
<211> LENGTH: 41
<212> TYPE: DNA
<213> ORGANISM: Artificial Sequence
<220> FEATURE:
<223> OTHER INFORMATION: Adapter Oligonucleotide

<400> SEQUENCE: 5
acgttagcca ccatacttga gtgatgacgg tttttcattg c                      41

<210> SEQ ID NO 6
<211> LENGTH: 43
<212> TYPE: DNA
<213> ORGANISM: Artificial Sequence
<220> FEATURE:
<223> OTHER INFORMATION: Adapter Oligonucleotide

<400> SEQUENCE: 6
actgatccgc actaacgact gctttgctag ttgcctcaga cat                    43

<210> SEQ ID NO 7
<211> LENGTH: 35
<212> TYPE: DNA
<213> ORGANISM: Artificial Sequence
<220> FEATURE:
<223> OTHER INFORMATION: Detection Probe
<220> FEATURE:
<221> NAME/KEY: misc_feature
<222> LOCATION: 1
<223> OTHER INFORMATION: T is labeled with dabcyl
<220> FEATURE:
<221> NAME/KEY: misc_feature
<222> LOCATION: 15
<223> OTHER INFORMATION: T is labeled with Rhodamine

<400> SEQUENCE: 7
tagtgcccga gcactacgtt agccaccata cttga                             35

<210> SEQ ID NO 8
<211> LENGTH: 36
<212> TYPE: DNA
<213> ORGANISM: Artificial Sequence
<220> FEATURE:
<223> OTHER INFORMATION: Detection Probe
<220> FEATURE:
<221> NAME/KEY: misc_feature
<222> LOCATION: 1
<223> OTHER INFORMATION: T is labeled with fluoroscein
<220> FEATURE:
<221> NAME/KEY: misc_feature
<222> LOCATION: 15
```

<223> OTHER INFORMATION: T is labeled with dabcyl

<400> SEQUENCE: 8
tagcacccga gtgctaactg atccgcacta acgact                                    36

<210> SEQ ID NO 9
<211> LENGTH: 58
<212> TYPE: DNA
<213> ORGANISM: Artificial Sequence
<220> FEATURE:
<223> OTHER INFORMATION: Internal Amplification Control

<400> SEQUENCE: 9
aatcaaaagc gaatgcgtat gtctgaggca actagcaaag ctgcaaaaga tgaagaag           58

<210> SEQ ID NO 10
<211> LENGTH: 40
<212> TYPE: DNA
<213> ORGANISM: Artificial Sequence
<220> FEATURE:
<223> OTHER INFORMATION: Amplification Primer

<400> SEQUENCE: 10
cgtctccagt ccagacttct cgggaatcaa aagcgaatgc                                40

<210> SEQ ID NO 11
<211> LENGTH: 42
<212> TYPE: DNA
<213> ORGANISM: Artificial Sequence
<220> FEATURE:
<223> OTHER INFORMATION: Amplification Primer

<400> SEQUENCE: 11
cgtctaccgt ccagacttct cgggaatcaa aagcgaatgc gc                             42

<210> SEQ ID NO 12
<211> LENGTH: 42
<212> TYPE: DNA
<213> ORGANISM: Artificial Sequence
<220> FEATURE:
<223> OTHER INFORMATION: Amplification Primer

<400> SEQUENCE: 12
actacgtcga atgcatgtct cgggacttct tcatcttttg cc                             42

<210> SEQ ID NO 13
<211> LENGTH: 43
<212> TYPE: DNA
<213> ORGANISM: Artificial Sequence
<220> FEATURE:
<223> OTHER INFORMATION: Amplification Primer

<400> SEQUENCE: 13
actacgtcga atgcatgtct cgggagcttc ttcatctttt gcc                            43

<210> SEQ ID NO 14
<211> LENGTH: 12
<212> TYPE: DNA
<213> ORGANISM: Artificial Sequence
<220> FEATURE:
<223> OTHER INFORMATION: Bumper Primer

<400> SEQUENCE: 14
ccgcagcata cg                                                              12

-continued

```
<210> SEQ ID NO 15
<211> LENGTH: 14
<212> TYPE: DNA
<213> ORGANISM: Artificial Sequence
<220> FEATURE:
<223> OTHER INFORMATION: Bumper Primer

<400> SEQUENCE: 15
ccgcagcata cgcg                                                       14

<210> SEQ ID NO 16
<211> LENGTH: 14
<212> TYPE: DNA
<213> ORGANISM: Artificial Sequence
<220> FEATURE:
<223> OTHER INFORMATION: Bumper Primer

<400> SEQUENCE: 16
ttgcgcatat gctt                                                       14

<210> SEQ ID NO 17
<211> LENGTH: 15
<212> TYPE: DNA
<213> ORGANISM: Artificial Sequence
<220> FEATURE:
<223> OTHER INFORMATION: Bumper Primer

<400> SEQUENCE: 17
ctttgatgat ttgcg                                                      15

<210> SEQ ID NO 18
<211> LENGTH: 41
<212> TYPE: DNA
<213> ORGANISM: Artificial Sequence
<220> FEATURE:
<223> OTHER INFORMATION: Adapter Oligonucleotide

<400> SEQUENCE: 18
acgttagcca ccatacttga gcaatgaaaa accgtcatca c                          41

<210> SEQ ID NO 19
<211> LENGTH: 60
<212> TYPE: DNA
<213> ORGANISM: Artificial Sequence
<220> FEATURE:
<223> OTHER INFORMATION: Internal Amplification Control

<400> SEQUENCE: 19
aatcaaaagc gaatgcgtat gtctgaggca actagcaaag cagtgcaaaa gatgaagaag       60

<210> SEQ ID NO 20
<211> LENGTH: 41
<212> TYPE: DNA
<213> ORGANISM: Artificial Sequence
<220> FEATURE:
<223> OTHER INFORMATION: Adapter Oligonucleotide

<400> SEQUENCE: 20
actgatccgc actaacgact gtgatgacgg tttttcattg c                          41

<210> SEQ ID NO 21
<211> LENGTH: 43
<212> TYPE: DNA
<213> ORGANISM: Artificial Sequence
<220> FEATURE:
<223> OTHER INFORMATION: Adapter Oligonucleotide
```

-continued

```
<400> SEQUENCE: 21
acgttagcca ccatacttga gctttgctag ttgcctcaga cat                    43

<210> SEQ ID NO 22
<211> LENGTH: 29
<212> TYPE: DNA
<213> ORGANISM: Artificial Sequence
<220> FEATURE:
<223> OTHER INFORMATION: Detection Probe
<220> FEATURE:
<221> NAME/KEY: misc_feature
<222> LOCATION: 1
<223> OTHER INFORMATION: T is labeled with dabcyl
<220> FEATURE:
<221> NAME/KEY: misc_feature
<222> LOCATION: 10
<223> OTHER INFORMATION: A is labeled with Rhoadamine

<400> SEQUENCE: 22
tccccgagta cgttagccac catacttga                                    29

<210> SEQ ID NO 23
<211> LENGTH: 29
<212> TYPE: DNA
<213> ORGANISM: Artificial Sequence
<220> FEATURE:
<223> OTHER INFORMATION: Detection Probe
<220> FEATURE:
<221> NAME/KEY: misc_feature
<222> LOCATION: 1
<223> OTHER INFORMATION: T is labeled with fluoroscein
<220> FEATURE:
<221> NAME/KEY: misc_feature
<222> LOCATION: 10
<223> OTHER INFORMATION: A is labeled with dabcyl

<400> SEQUENCE: 23
tccccgagta ctgatccgca ctaacgact                                    29
```

NEISSERIA GONORRHOEAE ASSAY

FIELD OF INVENTION

The present invention relates to nucleic acid amplification methods for the detection and/or quantitation of nucleic acid sequences of *Neisseria gonorrhoeae*. The present invention provides oligonucleotides that are complementary or that anneal to nucleic acid sequences of *Neisseria gonorrhoeae* for the amplification and/or detection of the same. The present invention also provides internal amplification controls (IACs) that can be used in nucleic acid amplification reactions to determine whether the assay conditions are permissible for amplification and/or detection of a target sequence. The present invention provides a diplex strand displacement amplification (SDA) assay for the amplification and/or detection of *Neisseria gonorrhoeae* nucleic acid sequences in the presence of an IAC.

BACKGROUND OF THE INVENTION

Gonorrhea is the most prevalent communicable disease reported in the United States, with an estimated 2.5 million or more cases reported annually. See Tierney et al., Current Medical Diagnosis and Treatment, 37$^{th}$ ed., 1998, Appleton & Lange. Gonorrhea is caused by *Neisseria gonorrhoeae*, a gram-negative diplococcus bacterium typically found inside polymorphonuclear cells, and is most commonly transmitted during sexual intercourse. These bacteria can infect the genital tract, the mouth and the rectum. In women, the opening to the uterus, the cervix, is the first site of infection. The incubation period of the bacterium is usually 2–8 days (see Tierney et al., Current Medical Diagnosis and Treatment, 37$^{th}$ ed., 1998, Appleton & Lange). Gonorrhea is an important cause of urethritis in men and cervicitis in women. Gonorrhea may spread into the uterus and fallopian tubes resulting in pelvic inflammatory disease ("PID") and in fact approximately 20% to 40% of PID and 14% of tubal infertility can be attributed to gonococcal infections. See Chan et al., 2000, Arch. Pathol. Lab. Med. 124:1649–1652.

Traditional laboratory diagnosis of gonorrhea is done by an overnight culture of clinical swabs (e.g., urine or cervical) obtained from a subject followed by biochemical and/or microscopic identification of *Neisseria gonorrhoeae*.

Recently, nucleic acid amplification tests have become widely used for detection and/or diagnosis. Currently available commercial *Neisseria gonorrhoeae* DNA amplification tests include PCR (Roche Molecular Systems, Branchburg, N.J.), and strand displacement amplification (SDA; Becton Dickinson, Sparks, Md.). In vitro nucleic acid amplification techniques provide powerful tools for detection and analysis of nucleic acids, especially when the target nucleic acids are present in small quantities. The sensitivity of such methods has made them particularly suitable in areas such as medical diagnosis (e.g., detection of infectious agents like bacteria and viruses, diagnosis of inherited and acquired genetic diseases, and the establishment of tissue type), isolation of genes, and forensic medicine (e.g., forensic tests for detection of specific nucleic acids in criminal investigations).

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392–396; Walker et al., 1992, Nuc. Acids. Res. 20:1691–1696; and EP 0 497 272, all of which are incorporated herein by reference), self-sustained sequence replication (3SR; Guatelli et al., 1990, Proc. Natl. Acad. Sci. USA 87:1874–1878), the Qβ replicase system (Lizardi et al., 1988, BioTechnology 6:1197–1202), and the techniques disclosed in WO 90/10064 and WO 91/03573. Examples of techniques that require temperature cycling are: polymerase chain reaction (PCR; Saiki et al., 1985, Science 230:1350–1354), ligase chain reaction (LCR; Wu et al., 1989, Genomics 4:560–569; Barringer et al., 1990, Gene 89:117–122; Barany, 1991, Proc. Natl. Acad. Sci. USA 88:189–193), transcription-based amplification (Kwoh et al., 1989, Proc. Natl. Acad. Sci. USA 86:1173–1177) and restriction amplification (U.S. Pat. No. 5,102,784).

The currently available nucleic acid amplification tests for *Neisseria gonorrhoea*, however, lack an internal control mechanism to assay for any inhibitory reaction conditions or human errors that are present in the tests and are thus prone to false negative results. Thus, there is a need for an assay that decreases the possibility of false negative results.

*Neisseria gonorrhoeae* shares a high degree of homology with other closely related *Neisseria* species. Thus, there is clearly a need for the development of new methods and oligonucleotides that are able to confirm the results of existing assays and/or increase the specificity and/or sensitivity of a test to detect *Neisseria gonorrhoeae*.

The present invention provides a diplex nucleic acid amplification assay which can be used as an alternative to the current monoplex *Neisseria gonorrhoeae* assay (i.e., no internal amplification control in the same reaction mixture with a target sequence). The present invention also provides oligonucleotides that can be used in both diplex and monoplex nucleic acid amplification assays designed to amplify and/or detect *Neisseria gonorrhoeae* nucleic acids.

Citation or discussion of a reference herein shall not be construed as an admission that such is prior art to the present invention.

SUMMARY OF THE INVENTION

The present invention provides a method for detecting qualitatively and/or quantitatively the presence or absence of *Neisseria gonorrhoeae* in a sample, said method comprising: (a) amplifying the target sequence using a first amplification primer having a sequence consisting essentially of the target binding sequence of any amplification primer disclosed herein and (b) detecting the amplified target sequence. The present invention also comprises the use of a second amplification primer consisting essentially of the target binding sequence of any amplification primer disclosed herein.

The present invention also provides Internal Amplification Control sequences in order to decrease the occurrence of false negative results.

The present invention also provides a method for detecting a *Neisseria gonorrhoeae* target sequence comprising: (a) hybridizing one or more amplification primers disclosed herein to a target sequence and (b) detecting said hybridized amplification primer.

The present invention also provides oligonucleotides which are useful in the amplification and detection of *Neisseria gonorrhoeae*. The present invention also provides kits comprising such oligonucleotides

BRIEF DESCRIPTION OF THE FIGURES

FIG. 1. The positions of the *Neisseria gonorrhoeae* genome to which the amplification primers, bumper primers and adapter oligonucleotides anneal.

DETAILED DESCRIPTION OF THE INVENTION

Any definitions provided are for reason of clarity and should not be considered as limiting. Except where noted, the technical and scientific terms used herein are intended to have the same meaning as commonly understood by one of ordinary skill in the art to which the invention pertains.

The present invention relates to nucleic acid amplification methods and assays for the detection and/or quantitation of nucleic acid sequences of *Neisseria gonorrhoeae*. The present invention provides one or more oligonucleotides that are complementary or that anneal to nucleic acid sequences of *Neisseria gonorrhoeae* for the amplification and/or detection of said sequences. The present invention further provides an internal amplification control (IAC) that can be used in nucleic acid amplification assays of the invention to determine whether the assay conditions are permissible for amplification and/or detection of a target sequence. The oligonucleotides may be used in all types of amplification reactions such as, for example, Strand Displacement Amplification (SDA), Polymerase Chain Reaction (PCR), Ligase Chain Reaction, Nucleic Acid Sequence Based Amplification (NASBA), Rolling Circle Amplification (RCA), Transcription Mediated Amplification (TMA) and Qβ Replicase-mediated amplification.

The methods of the invention are particularly advantageous over traditional methods used for the detection of gonorrhoeae, as they reduce false negative results by, for example, inclusion of internal amplification controls.

Sensitivity of an assay relates to the tolerance of false negatives. A test result is false negative if the test shows negative but the sample actually contains the target sequence. The smaller amount the target sequence an assay can detect, the higher sensitivity an assay has.

Specificity of an assay relates to the tolerance of false positives. A test result is false positive if the test shows positive but the sample actually does not contain the target sequence. Thus, a more specific an assay should have lower level of false positives.

In accordance with the present invention, a result of an assay to detect for *Neisseria gonorrhoeae* in a sample that utilizes an IAC can be interpreted as described in Table 1.

TABLE 1

Interpretation of a diplex SDA assay

| | Result | | | |
|---|---|---|---|---|
| IAC | + | − | + | − |
| Target Sequence for *Neisseria gonorrhoeae* | − | + | + | − |
| Presence or absence of *Neisseria gonorrhoeae* | absence | presence | presence | inhibitory reaction, assay need to be re-performed or modified |

In accordance with the present invention, an IAC may be used instead of, and/or in addition to, a conventional amplification control (AC). It is understood by one skilled in the art that the conventional AC reaction is performed in a separate reaction mixture from the sample to be tested. A conventional AC reaction comprises amplification reagents and target DNA. If the amplification and/or detection of the target DNA in the AC reaction is suppressed, an indication that the target sequence is absent from a test sample may be attributed to inhibitory signals in the reaction. While this form of control reaction is effective, it is not the most desirable. Since the AC reaction is performed separately, it cannot exactly reflect the conditions of the reactions containing the test sample. The methods of the invention are particularly useful in that they have an IAC and the control reaction is performed under identical spatial and temporal conditions as the amplification and/or detection of the target sequence thereby minimizing human error.

The present invention also provides amplification primers that anneal to both a target sequence (i.e., a sequence of *Neisseria gonorrhoeae*) and/or an IAC sequence. In some embodiments of the invention a bumper primer or adapter oligonucleotide or its respective target binding sequence described in Table 2, Table 3 or FIG. 1 may be used as an amplification primer. In some embodiments of the invention, an amplification primer is chosen from the amplification primers described in Table 2, Table 3 or FIG. 1 as disclosed herein. In another embodiment of the invention, an amplification primer is chosen from the target binding sequences of amplification primers described in Table 2, Table 3 or FIG. 1 as disclosed herein. In another embodiment of the invention, the amplification primers comprise GCINT3-APL2 (SEQ ID NO:1) and GCINT3-APR1 (SEQ ID NO: 2).

The present invention further provides adapter oligonucleotides and detection probes that can be used in a nucleic acid amplification assay for the detection of nucleic acid sequences of *Neisseria gonorrhoeae*. In some embodiments of the invention, the adapter oligonucleotide is a single-stranded oligonucleotide comprising SEQ ID NO:5, 6, 18, 20 or 21. In other embodiments of the invention, the detection probe is a single-stranded oligonucleotide comprising SEQ ID NO: 7, 8, 22 or 23, and a fluorescent donor/quencher pair linked to the oligonucleotide.

Amplification Methods

The oligonucleotides disclosed herein can be used in any method of nucleic acid amplification known in the art.

Suitable amplification methods include, but are not limited to, Polymerase Chain Reaction ("PCR"; see U.S. Pat. Nos. 4,683,195; 4,683,202; 4,800,159; and 4,965,188), Strand Displacement Amplification ("SDA"; see Walker et al., *Proc. Nat'l Acad. Sci. USA* 89:392 (1992); Walker et al., *Nucl. Acids Res.* 20:1691 (1992); and U.S. Pat. No. 5,270,184, the disclosure of which is hereby incorporated in its entirety by reference), thermophilic Strand Displacement Amplification ("tSDA"; see EP 0 684 315), Self-Sustained Sequence Replication ("3SR"; see Guatelli et al., *Proc. Nat'l Acad. Sci. USA* 87:1874–78 (1990)), Nucleic Acid Sequence-Based Amplification ("NASBA"; see U.S. Pat. No. 5,130,238), Qβ replicase system (see Lizardi et al., *BioTechnology* 6:1197 (1988)); Ligase Chain Reaction ("LCR"; see U.S. Pat. No. 5,427,930); Rolling Circle Amplification (see Lizardi et al., *Nat Genet* 19:225–232 (1998)) and transcription based amplification (see Kwoh et al., *Proc. Nat'l Acad. Sci. USA* 86:1173–77 (1989)). The amplification primers of the present invention may be used to carry out PCR, SDA or tSDA..

SDA generally proceeds along the following pathway. First, amplification primers bind to a target sequence or to a displaced single-stranded extension product that has been previously polymerized. Second, a 5'–3' exonuclease-deficient polymerase incorporates an α-thiodeoxynucleoside triphosphate ("α-thio dNTP") into an extension product. If the α-thio dNTP is α-thio dCTP, for example, it is incorporated into the extension product wherever there is a complementary G residue in the template. Incorporation of an α-thio dNTP into the extension product at a restriction endonuclease recognition site creates a hemimodified site, i.e. a site modified only on the extension product strand. A restriction endonuclease then nicks the hemimodified double-stranded restriction site. Next, the restriction endonuclease dissociates from the nick site. Finally, a polymerase that is deficient in 5'–3' exonuclease activity extends from the 3' end of the nick and displaces the downstream strand of DNA. Nicking, strand extension and strand displacement occur concurrently and continuously because extension from the nick regenerates another nickable restriction site. When a pair of amplification primers is used that each hybridize to one of the two strands of a double-stranded duplex comprising a target sequence, amplification is exponential because both the sense and antisense strands serve as templates in each round of amplification. When a single amplification primer is used, amplification is linear because only one strand serves as a template for primer extension. Examples of restriction endonucleases that nick their double-stranded recognition sites when an α-thio dNTP is incorporated and that are suitable for SDA include BsoB1, BsrI, BstNI, BsmAI, BstOI, BslI, AvaI, HincII and NciI. SDA is further described in U.S. Pat. Nos. 5,270,184, 5,455,166 and 5,648,211, which are incorporated by reference herein in their entirety. A SDA assay can be, but is not limited to, a traditional (or conventional) SDA (as described in Walker et al., PNAS (1992) 89:392–396, U.S. Pat. Nos. 5,962,273, 5,712,124, and 5,744,311, each of which is incorporated herein by reference), a thermophilic SDA (as described in Walker et al., Nuc. Acids Res. (1992) 20:1691–1696, U.S. Pat. Nos. 5,648,211 and 5,744,311, each of which is incorporated herein by reference), and a homogeneous real time fluorescent thermophilic SDA (as described in U.S. Pat. No. 6,379,888, which is incorporated herein by reference).

Cross-contamination with amplification products carried over from previous amplification reactions in reagents, pipetting devices and laboratory surfaces may be reduced by incorporating various residues into extension products. For example, thymine may be substituted with 2'-deoxyuridine 5' triphosphate ("dU"), as is taught in EP 0 624 643. Excision of dU that is incorporated into amplification products is catalyzed by uracil DNA glycosylase ("UDG"), which renders amplification products containing dU incapable of further amplification. The UDG itself may be inactivated when appropriate to continue amplification.

In the case of tSDA, primers and their target sequences preferably are selected such that their GC content is less than 70% of the total nucleotide composition to minimize secondary structure and primer-primer interactions that may limit target amplification efficiency. A suitable amplification primer for tSDA comprises, in order from the 3' end of the probe to the 5' end, a target binding sequence, a restriction endonuclease recognition site, and a "tail." The target binding sequence hybridizes specifically to a complementary sequence of the target nucleic acid. The restriction endonuclease recognition site is recognized by a restriction endonuclease that nicks one strand of a DNA duplex when the recognition site is hemimodified, as described by Walker et al., *Proc. Nat'l Acad. Sci. USA* 89:392 (1992) and Walker et al., *Nucl. Acids. Res.* 20:1691 (1992). The 5' tail functions as a polymerase repriming site when the remainder of the amplification primer is nicked and displaced during tSDA. The repriming function of the tail sustains the tSDA reaction and allows synthesis of multiple amplicons from a single target molecule. The length and sequence of the tail region may vary, provided that the tail remains hybridized to the target after nicking and that the tail does not contain sequences that will hybridize either to the target binding sequence or to other primers.

Some amplification methods, such as tSDA, use a "bumper primer" or "external primer" to displace primer extension products. A "bumper primer" or "external primer" is a primer used to displace an amplification primer and its extension product in an amplification reaction. A bumper primer anneals to a target sequence upstream of an amplification primer such that extension of the bumper primer displaces the downstream amplification primer and its extension product. Primer extension products alternatively may be displaced by heating. Bumper primers used in SDA and tSDA reactions need not hybridize specifically to enterovirus nucleic acids. Rather, bumper primers may hybridize to any target sequence that is upstream from the amplification primers and that is sufficiently close to the binding site of the amplification primer to displace the amplification primer extension product upon extension of the bumper primer. Mismatches between the bumper primer sequence and its target sequence generally do not affect amplification efficiency, provided the bumper primer still hybridizes to the its target sequence. Furthermore, the specificity of the SDA system for amplification of the target sequence in preference to other nucleic acids is not dependent upon the specificity of the bumper primer(s) for hybridization to the target nucleic acid. The specificity of an SDA system for the target sequence is derived from the fidelity of hybridization of the SDA primers and probes or oligonucleotides used for detection of amplified products.

When an amplification reaction used in accordance with the invention is a tSDA reaction, the polymerases that can be used include, but are not limited to, exo⁻ Vent (New England Biolabs), exo⁻ Deep Vent (New England Biolabs), Bst (BioRad), exo⁻ Pfu (Stratagene), Bca (Panvera), and Sequencing Grade Taq (Promega). Others may be routinely identified using the foregoing extension assay. The polymerases Tth (Boehringer), Tfi (Epicentre), REPLINASE (DuPont) and REPLITHERM (Epicentre) are able to displace a strand from a nick, but they also have 5'–3' exonuclease activity. These polymerases are useful in the methods of the invention after removal of the exonuclease activity, e.g., by genetic engineering. As the thermostability of thermophilic restriction endonucleases is generally limited to less than 65° C., thermophilic polymerases with optimal activity around this temperature or lower (e.g., Bst and Bca) are more compatible with thermophilic restriction endonucleases in the reaction.

The components of the present invention may be optimized to a form where each component could be dried and rehydrated when needed by using any technique known in the art. (See Little et al., Clinical Chemistry 45(6):777–784 (1999), which is incorporated herein by reference).

Primer Design

An "amplification primer" is an oligonucleotide for amplification of a target sequence by extension of the oligonucleotide after hybridization to a target sequence or by ligation of multiple oligonucleotides that are adjacent when hybridized to the target sequence. At least a portion of the amplification primer hybridizes to the target sequence. This portion is referred to as the target binding sequence and it determines target-specificity of the primer. It should be understood that the target binding sequences exemplified in the present invention may also be used in a variety of other ways for detection of *Neisseria gonorrhoea*. For example, the target binding sequences disclosed herein may alternatively be used as hybridization probes for direct detection of *Neisseria gonorrhoeae,* either without prior amplification or in a post amplification assay. Such hybridization methods are well known in the art and typically employ a detectable label associated with or linked to the target binding sequence to facilitate detection of hybridization.

The design of amplification primers may be optimized for each method of amplification. As no special sequences or structures are required to drive the amplification reaction, amplification primers for a Polymerase Chain Reaction (PCR) may consist only of template binding sequences. However, other amplification reactions require specialized nucleotide sequences, in addition to the target binding sequence, in order for the reaction to proceed. For example, an amplification primer for use in a SDA assay further comprises a restriction endonuclease recognition site 5' to the target binding sequence (see U.S. Pat. Nos. 5,455,166 and 5,270,184). The amplification primer may also comprise a 3'-OH group, which is extendable by DNA polymerase when the template-binding sequence of the amplification primer is annealed to the target sequence. Amplification primers for Self-sustained Sequence Replication (3SR) and Nucleic Acid Sequence-Based Assay (NASBA), in contrast, comprise an RNA polymerase promoter near the 5' end. (3SR assays are described in Guatelli et al., 1990, Proc. Natl. Acad. Sci. USA 87:1874–1878) The promoter is appended to the target binding sequence and serves to drive the amplification reaction by directing transcription of multiple RNA copies of the template. Such sequences in additional to the target binding sequence that are necessary for a particular amplification reaction are well known in the art. a promoter recognized by RNA polymerase for self-sustained replication assays In designing the amplification primers and the bumper primers of the present invention, general concerns known in the art should be taken into account. For example, when a target sequence comprising a large number of GC and AT repeats is used for designing a primer, cares should be taken to minimize potential dimer interactions to avoid self-hybridization of primers. Primers that can form four or more consecutive bonds with itself, or eight or more inter-strand bonds with other primers should be generally avoided. Primers that can form 3' dimers should especially be avoided, because hybridizing at the 3' ends of the primer, even transiently, will lead to extension of the primer due to polymerase action and ruining of the primer. Certain computer software programs (e.g., Oligo™, National Biosciences, Inc., Plymouth, Minn.) can be used in designing of the primers to avoid the problems. Primer combinations are also screened for optimal conditions.

As is known in the art, annealing or hybridization of complementary and partially complementary nucleic acid sequences may also be obtained by adjustment of the reaction conditions to increase or decrease stringency (e.g., adjustment of temperature or salt content of the buffer). Such modifications of the disclosed sequences and any necessary adjustments of conditions are encompassed by the present invention. Information relating to buffer conditions can be found in Experimental Design in Biotechnology by Dr. Perry Haaland (Marcell Dekker, NY, 1989), incorporated herein by reference in its entirety.

In a diplex amplification reaction, an amplification primer is designed to be able to hybridize to both a *Neisseria gonorrhoeae* target sequence and an IAC sequence and amplify the sequence to which it is hybridized. This is achieved by using a shared nucleic acid sequence between *Neisseria gonorrhoeae* target sequence and an IAC sequence to design an amplification primer. Other sequences, as required for performance of a selected amplification reaction, may optionally be added to an amplification primer as disclosed herein.

By way of example, but not limitation, amplification primers for use in a SDA assay generally comprise a 3' template-binding sequence, a nickable restriction endonuclease recognition site 5' to the template-binding sequence, and a tail sequence about 10–25 nucleotides in length 5' to the restriction endonuclease recognition site. Such amplification primer may contain a recognition site for the restriction endonuclease BsoBI, which is nicked during the SDA reaction. It will be apparent to one skilled in the art that other nickable restriction endonuclease recognition sites may be substituted for the BsoBI recognition site. The amplification primer may also contain a tail sequence (5' to the restriction endonuclease recognition site). The tail sequence should not contain the restriction site used for SDA and sequences which will anneal either to its own target binding sequence or to the other primers (e.g., bumper primers).

In some embodiments, a pair of amplification primers is used, each of which anneals to one of the two strands of a double stranded target sequence or IAC sequence. In this case, amplification is exponential because both the sense and antisense strands serve as templates for the opposite primer in subsequent rounds of amplification. When a single amplification primer is used, amplification is linear because only one strand serves as a template for primer extension.

In some embodiments, the methods of the present invention encompass an amplification primer that comprises a nucleotide sequence consisting essentially of SEQ ID NO: 1, 2, 10, 11, 12, 13 or their respective target binding sequences. In other embodiments, the methods of the present invention encompass at least two amplification primers, wherein a first amplification primer comprises a nucleotide sequence consisting essentially of SEQ ID NO: 1, 10, 11 or their respective target binding sequences; and a second amplification primer comprises a nucleotide sequence consisting essentially of SEQ ID NO: 2, 12, 13 or their respective target binding sequences.

In some embodiments, the methods of the present invention encompasses one or more bumper primers. A bumper primer is a primer used to displace an amplification primer and its extension product in an amplification reaction. A bumper primer anneals to a target sequence upstream of an amplification primer, such that extension of the bumper primer displaces the downstream amplification primer and its extension product. A bumper primer may also function as an amplification primer. In some embodiments, the methods of the present invention encompass one or more bumper primers. In certain embodiments, the bumper primer comprises an oligonucleotide having the sequence comprising SEQ ID NO: 3, 4, 14, 15, 16 or 17. In one embodiment, a bumper primer comprises an oligonucleotide having a partial or complete sequence of SEQ ID NO: 3, 4, 14, 15, 16 or 17. In another embodiment, the methods of the present invention encompass at least two bumper primers, wherein a first primer comprises a nucleotide sequence consisting essentially of SEQ ID NO: 3, 14, or 15, and a second primer comprises a nucleotide sequence consisting essentially of SEQ ID NO: 4, 16, or 17.

Target Sequences

"Target" or "target sequence" refers to a *Neisseria gonorrhoeae* nucleic acid sequence to be amplified and/or detected. A target or target sequence includes the *Neisseria gonorrhoeae* nucleic acid sequence to be amplified and any complementary second strand. In some embodiments, a target sequence may be single-stranded or double-stranded, in which case, either one or both strands can bind to an amplification primer. A target or target sequence may also comprise a nucleotide sequence that is recognized by an adapter oligonucleotide (i.e., adapter-binding sequence).

The primers of the present invention are designed to anneal to a region of *Neisseria gonorrhoeae* genomic DNA illustrated in FIG. 1. (see U.S. Pat. No. 5,962,273, which is incorporated herein by reference in its entirety).

Internal Amplification Control

"Internal amplification control", "IAC" or "IAC sequence" refers to a nucleic acid sequence comprising a sequence that anneals to an amplification primer and a sequence that can be detected separately from the target sequence. Any detection method known in the art may be employed.

In accordance with the present invention, an IAC sequence is designed to share nucleic acid sequences with a *Neisseria gonorrhoeae* target sequence, thus the same amplification primer(s) can amplify both an IAC sequence and a target sequence if it is present in a sample. An IAC sequence is also designed to have some nucleic acid sequences that differ from a *Neisseria gonorrhoeae* target sequence, so that the detection of the IAC sequence and the target sequence may be differentiated. Since an IAC sequence is amplified and/or detected in the same reaction mixture as a target sequence, diplex assays have the advantage of detecting human error or an inhibitory reaction condition, e.g., the presence of an inhibitor or absence of a critical reagent. The presence of an IAC in the same reaction as the sample to be tested eliminates the need for separate amplification control reactions as required by the current monoplex SDA assays.

Although not intending to be bound by a particular mechanism of action, the presence of an IAC in the same reaction as a target sequence allows the amplification assay of the present invention to detect the presence of inhibitors of the reaction and/or conditions that may indicate a false negative result. As used herein, a false negative result refers to a result that indicates no detection of a target sequence, however, such indication is not due to the absence of the target sequence in the sample, but due to human error or a reaction condition, e.g., the lack of a critical reaction element, or the existence of an inhibitor of the reaction, or a mistake in performing the assay.

A detection method is used wherein such method differentiates amplification products of a target sequence from amplification products of an IAC sequence. In one embodiment, the amplification products of the target sequence and the IAC may be detected by different dye labeled detection probes. In another embodiment, fluorescein is used to detect amplification products of the target sequence and rhodamine fluorescence is used to detect the amplification products of the IAC.

In some embodiments, an IAC sequence is designed such that either its 3' or 5' terminus contains a sequence in common with a *Neisseria gonorrhoeae* DNA sequence. In some other embodiments, an IAC is designed such that both the 3' and 5' terminus contain sequences in common with a *Neisseria gonorrhoeae* DNA sequence for an amplification primer to bind.

An IAC sequence is also designed to comprise a nucleic acid sequence that is different from the *Neisseria gonorrhoeae* target sequence to be amplified, such that the detection of the amplification products of the IAC and the target sequence can be differentiated.

In some embodiments, the methods of the present invention utilize an IAC that comprises a nucleotide sequence consisting essentially of SEQ ID NO: 9 or 19.

Detection of Nucleic Acids

The amplification products generated using one or more primers of the invention can be detected by any method known in the art. As used herein, amplification products include both the amplified target sequences and the amplified IAC sequences. Amplification products can be detected by hybridization to a labeled probe using conventional techniques, for example, one that hybridizes to amplified nucleic acids at a sequence that lies between the amplification primers. Alternatively, amplification products may be detected by their characteristic size, for example by electrophoresis followed by ethidium bromide staining to visualize the nucleic acids. In a further alternative, a labeled amplification primer is used. In a still further alternative, a labeled amplification primer/internal probe is extended on the target sequence, as described by Walker et al., Proc. Nat'l Acad. Sci. USA 89:392 (1992); or Walker et al., Nucl. Acids Res. 20:1691 (1992). In another embodiment, detection is accomplished directly through hybridization and extension of a labeled reporter probe as described in U.S. Pat. Nos. 5,928,869 and 5,958,700. Detection methods also include a chemiluminescent method in which amplified products are detected using a biotinylated capture probe and an enzyme-conjugated detector probe, as described in U.S. Pat. No. 5,470,723. After hybridization of these two probes at different sites between the two amplification primer binding sites, the complex is captured on a streptavidin-coated microtiter plate, and the chemiluminescent signal is developed and read in a luminometer.

In an embodiment of the present invention, the detection method should detect both the target and the IAC amplification products, and differentiate between the amplification products detected. Any method known in the art capable of achieving this purpose can be used. For example, the detection methods that are disclosed in Walker et al., Nucl. Acids Res., (1992) 20:1691–1696, the U.S. Pat. Nos. 5,648,211, 5,962,273, 5,814,490, 5,928,869, 6,316,200, and European Patent EP 0 678 582 (each of which is incorporated herein by reference) can be used in accordance with the present invention. In another embodiment, universal probes and methods for detection of nucleic acids are used (see U.S. Pat. No. 6,379,888, which is incorporated herein by reference).

In one embodiment, the universal detection method employs an adapter oligonucleotide and a detection probe for detection of a target sequence (a target sequence, an IAC sequence, or extension products thereof). The adapter oligonucleotide comprises a 3' target binding sequence and a 5' sequence. The complement of the 5' sequence, produced by amplification, will hybridize and extend off of the detection probe. Such hybridization can than be detected as an indication of a successful amplification reaction.

At least two different adapter oligonucleotides may be used to simultaneously detect different target sequences (e.g., amplification products of a target sequence and amplification products of an IAC sequence). In this case, the 5' adapter sequence of the adapter oligonucleotide is different for each template to be detected. By labeling detection probes which indicate the presence of target sequence and IAC with different fluorescent labels (e.g., different donor/quencher dye pairs), the presence of each can be determined by detecting changes in the extent of fluorescence quenching in each of the detection probes.

In some embodiments, adapter oligonucleotides and detection probes are used for the detection of the amplification products of an IAC and a target sequence. The portion of the IAC sequence that can be recognized by an adapter oligonucleotide is designed to be different from the portion of the target sequence that can be recognized by an adapter oligonucleotide, i.e., the adapter oligonucleotide that recognizes the IAC sequence and the adapter oligonucleotide that recognizes the target sequence have, inter alia, different template-binding sequences. The specificity of the adapter oligonucleotides (with respect to the IAC sequence and the target sequence) ultimately leads to the detection of different amplification products (of an IAC or of a target sequence) by different detection probes.

In one embodiment, multiple adapter oligonucleotides per strand of template may be employed if desired, each hybridizing to the target sequence downstream of the other on the same strand, with all adapter oligonucleotides being hybridized downstream of the amplification primer. In this manner, each adapter oligonucleotide is displaced by extension of the upstream adapter oligonucleotide and the most 5' adapter oligonucleotide is displaced by the amplification primer. Use of multiple adapter oligonucleotides has the advantage of increasing or amplifying the signal generated per target sequence, with an increase in sensitivity of the assay.

Many donor/quencher dye pairs known in the art are useful in the present invention. These include, but not limited to, for example, fluorescein isothiocyanate (FITC)/ tetramethylrhodamine isothiocyanate (TRITC), FITC/Texas Red.TM. (Molecular Probes), FITC/N-hydroxysuccinimidyl 1-pyrenebutyrate (PYB), FITC/eosin isothiocyanate (EITC), N-Docket hydroxysuccinimidyl 1-pyrenesulfonate (PYS)/ FITC, FITC/Rhodamine X, FITC/tetramethylrhodamine (TAMRA), and others. The selection of a particular donor/quencher pair is not critical. For energy transfer quenching mechanisms it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl) aminonaphthalene (EDANS). Any dye pair which produces fluorescence quenching in the detection probe of the invention can be used in the methods of the invention, regardless of the mechanism by which quenching occurs. Terminal and internal-labeling methods are also known in the art and may be routinely used to link the donor and quencher dyes at their respective sites in the detection probe.

In some embodiments, the methods of the present invention utilize an adapter oligonucleotide that comprises a nucleotide sequence consisting essentially of SEQ ID NO: 5, 6, 18, 20 or 21.

The present invention provides detection probes that are single-stranded oligonucleotides comprising SEQ ID NO: 7, 8, 22 or 23, and a label. In certain embodiments, the label comprises at least one fluorescent donor/quencher pair linked to the oligonucleotide, wherein the fluorescent moiety is rhodamine, fluorescein or dabcyl.

In some embodiments, the present invention provides diplex homogeneous real time fluorescent thermophilic SDA (tSDA). Homogeneous real time fluorescent thermophilic SDA is a modified tSDA which detects nucleic acid target sequences by fluorescence quenching mechanisms (see, e.g., U.S. Pat. No. 6,379,888, which is incorporated herein by reference in its entirety). For example, in one embodiment, a detection probe may comprise a fluorescent donor/acceptor pair so that fluorescence quenching occurs in the absence of a target sequence. Although not intending to be bound by a particular mechanism of action, in the absence of hybridization of the detection probe to a second oligonucleotide (which is produced by amplification of a target sequence), the probe adopts a conformation which brings the donor and quencher into close spatial proximity and results in quenching of donor fluorescence. The probe may fold into an ordered secondary structure (e.g., a G-quartet, hairpin or triple helix), into a random coil, or into any other conformation which brings the donor and quencher into close enough proximity to produce fluorescence quenching. However, when the detection probe hybridizes to a second oligonucleotide, the intramolecularly base-paired secondary structure of the detection probe becomes unfolded or linearized, which increases the distance between the donor and the quencher and thereby reducing or eliminating fluorescence quenching. Alternatively, the detection probe may be designed as a linear detection probe (i.e., it does not fold into a secondary structure), wherein the distance between the donor and the quencher is short enough to produce fluorescence quenching. In this case (and optionally in cases where a non-linear detection probe described herein is used), the detection probe also contains a restriction endonuclease recognition site (RERS) between the fluorescent donor/quencher pair. The intermolecular base-pairing between the detection probe and a second oligonucleotide renders the RERS double-stranded and thereby cleavable or nickable by a restriction endonuclease. Although not intending to be bound by a particular mechanism of action, cleavage or nicking by the restriction endonuclease separates the donor and acceptor onto separate nucleic acid fragments, which leads to decreased quenching.

An associated change in a fluorescence parameter (e.g., an increase in donor fluorescence intensity, a decrease in acceptor fluorescence intensity or a ratio of the donor and/or acceptor fluorescence intensities) may be monitored in accordance with the methods of the invention to detect and/or monitor the presence of the target sequence. Monitoring a change in donor fluorescence intensity is usually preferred, as this change is typically larger than the change in acceptor fluorescence intensity. Other fluorescence parameters such as a change in fluorescence lifetime may also be monitored in accordance with the invention.

Kits

The present invention also provides kits for amplification and/or detection of *Neisseria gonorrhoeae* nucleic acids comprising one or more amplification primers consisting essentially of SEQ ID NOS:1, 2, 10, 11, 12, 13 or their respective target binding sequences and at least one container which contains such primers. The kit may optionally include any one or more of: an IAC, adapter oligonucleotides, or detection probes. The kit may further include other components and reagents for performing a hybridization or amplification reaction, such as a Southern hybridization, dot blot hybridization, PCR, or SDA. For detection by hybridization, a appropriate solution to perform hybridization may be included, e.g., 0.3 M NaCl, 0.03 M sodium citrate, 0.1% SDS. Components for detection methods also may be included in the kit, e.g., a second probe, a radiolabel, an enzyme substrate, an antibody and the like. Reagents appropriate for use with a nucleic acid amplification method also may be included. The components of the kit are packaged together in a common container, typically including instructions for performing selected specific embodiments of the methods disclosed herein.

EXAMPLES

Example 1

Design of SDA Primer Sets

A portion of the *Neisseria gonorrhoeae* genome has been sequenced and characterized for targeting by amplification assays (see U.S. Pat. No. 5,962,273, incorporated herein by reference in its entirety). For purpose of this assay, a portion of the *Neisseria gonorrhoeae* genome that had not previously been targeted for amplification assays was selected for targeting. This sub-region of the *Neisseria gonorrhoeae* genome was analyzed in current GenBank and SeqWeb databases for *Neisseria gonorrhoeae* specificity.

Amplification primers were designed to amplify both *Neisseria gonorrhoeae* target sequences and an IAC. Multiple versions of the primers were designed as shown in Table 2 and 3. The positions of the regions of the *Neisseria gonorrhoeae* genome to which the selected oligonucleotides (amplification primers, bumper primers, and adapter oligonucleotides) anneal are illustrated in FIG. 1.

TABLE 2

Primary Oligonucleotides of SDA Assays for Amplification and/or Detection of *Neisseria gonorrhoeae*

| Oligonucleotide | Sequence | |
|---|---|---|
| Amplification Primers: | | |
| GCINT3-APL2 | 5'CGTCTCCAGTCCAGACTT*CTCGGG*AATCAAAAGCGAATGCG3' | (SEQ ID NO:1) |
| GCINT3-APR1 | 5'ACTACGTCGAATGCATGT*CTCGGG*ACTTCTTCATCTTTTGC3' | (SEQ ID NO:2) |
| Bumpers: | | |
| GCINT3-BL2 | 5'CCGCAGCATACGC3' | (SEQ ID NO:3) |
| GCINT3-BR3 | 5'TGCGCATATGCTTTG3' | (SEQ ID NO:4) |
| Adapter Oligonucleotides: | | |
| GC3A-R1 | 5'ACGTTAGCCACCATACTTGAGTGATGACGGTTTTTCATTGC3' | (SEQ ID NO:5) |
| ICAdpt9 | 5'ACTGATCCGCACTAACGACTGCTTTGCTAGTTGCCTCAGACAT3' | (SEQ ID No. 6) |
| GC3A-R2 | 5'ACTGATCCGCACTAACGACTGTGATGACGGTTTTTCATTGC3' | (SEQ ID NO:20) |
| ICAdpt10 | 5'ACGTTAGCCACCATACTTGAGCTTTGCTAGTTGCCTCAGACAT3' | (SEQ ID NO:21) |
| Detection probes: | | |
| CTGCUnv3 | 5'(Dabcyl)-TAGTGC*CCGAGC*AC(Rhodamine)-TACGTTAGCCACCATACTTGA3' | (SEQ ID NO:7) |
| ICUnv4 | 5'(Fluorescein)-TAGCA*CCCGAG*TGC(Dabcyl)-TAACTGATCCGCACTAACGACT3' | (SEQ ID NO:8) |
| MPC-DR | 5'(Dabcyl)-TC*CCCGAGT*-(Rhodamine)ACGTTAGCCACCATACTTGA3' | (SEQ ID NO:22) |
| MPC2-FD | 5'(Fluorescein)-TC*CCCGAGT*-(Dabcyl)ACTGATCCGCACTAACGACT3' | (SEQ ID NO:23) |
| IAC: | | |
| GCI3-IAC4 | 5'AATCAAAAGCGAATGCGTATGTCTGAGGCAACTGAGCAAAGCTGCAAAAGATGAAGAAG3' | (SEQ ID NO:9) |

Universal detection sequences are in bold and *Bso*B1 sites in italic.
Underlined represents target binding sequences.

TABLE 3

Additional Oligonucleotides of SDA Assays for Amplification and/or Detection of *Neisseria gonorrhoeae*

| Oligonucleotid | Sequence | |
|---|---|---|
| Amplification Primers: | | |
| GCINT3-APL1 | 5'CGTCTCCAGTCCAGACTT*CTCGGG*AATCAAAAGCGAATGC3' | (SEQ ID NO:10) |
| GCINT3-APL3 | 5'CGTCTACCGTCCAGACTT*CTCGGG*AATCAAAAGCGAATGCGC3' | (SEQ ID NO:11) |

TABLE 3-continued

Additional Oligonucleotides of SDA Assays for Amplification and/or Detection of *Neisseria gonorrhoeae*

| Oligonucleotid | Sequence | |
|---|---|---|
| GCINT3-APR2 | 5'ACTACGTCGAATGCATGT*CTCGGG*ACTTCTTCATCTTTTGCC3' | (SEQ ID NO:12) |
| GCINT3-APR3 | 5'ACTACGTCGAATGCATGT*CTCGGG*AGCTTCTTCATCTTTTGCC3' | (SEQ ID NO:13) |
| Bumpers: | | |
| GCINT3-BL1 | 5'<u>CCGCAGCATACG</u>3' | (SEQ ID NO:14) |
| GCINT3-BL3 | 5'<u>CCGCAGCATACGCG</u>3' | (SEQ ID NO:15) |
| GCINT3-BR1 | 5'<u>TTGCGCATATGCTT</u>3' | (SEQ ID NO:16) |
| GCINT3-BR2 | 5'<u>CTTTGATGATTTGCG</u>3' | (SEQ ID NO:17) |
| Adapter Oligonucleotides: | | |
| GC3A-F1 | 5'ACGTTAGCCACCATACTTGA<u>GCAATGAAAAACCGTCATCAC</u>3' | (SEQ ID NO:18) |
| IAC | | |
| IC3-IAC3 | 5'AATCAAAAGCGAATGCGTATGTCTGAGGCAACTAGCAAAGCAGTGCAAAAGATGAAGAAG3' | (SEQ ID NO:19) |

Universal detection sequences are in bold and BsoB1 sites are in italic.
Underlined represents target binding sequences.

Example 2

Optimization of SDA Reaction Conditions

Homogeneous real time fluorescent tSDA assays were performed to optimize the conditions for the assays of the invention. The oligonucleotides described in Table 2 and 3 were assayed to determine which oligonucleotides would provide optimal results. Concentrations of bicine and potassium hydroxide were also optimized. An example of optimized concentrations of the components of the SDA assay is as follows:

50 nM bumper (GCINT3-BL2 and BR3)
500 nM amplification primer (GCINT3-APL2 and APR1)
200 nM adapter (GC3A-R1 and ICADPT9)
200 nM detection probes (CTGCUnv3 and ICUnv4)
30 mM potassium phosphate
99.7mM bicine
58 mM potassium hydroxide
10% DMSO
9% glycerol
0.1 mM dATP, 0.1 mM dGTP, 0.25 mM dUTP and 0.35 mM S isomer of alpha thioated dCTP
5 mM magnesium acetate
100 ug/ml BSA
1.82% trehalose
360 uM DTT
15 BD units BsoB 1
6 BD units Bst Target DNA was lysed for 10 minutes at 114° C. in a BD Lyse Block. Samples were cooled for 10 minutes and 150 µl was transferred to priming wells to incubate for 20 minutes. 100 µl of the SDA priming mix was transferred to amplification microwells. The plates were then transferred into the BDProbeTec™-ET instrument for 60 minutes at 54° C.

Some oligonucleotides listed in Table 2 and Table 3 (e.g. APL 1 and APL2) were equivalent in performance, i.e., when these oligonucleotides were used in a SDA assay, the amount of amplification products detected are about the same (or the variation is within a statistical significance). However, GC3A-R1 provided a stronger detection signal as compared to GC3A-F1 when the same amount of target sequence was present. Amplification primers include GCINT3-APL2 (SEQ ID NO:1) and GCINT3-APR1 (SEQ ID NO:2). Bumper primers include GCINT3-BL2 (SEQ ID NO:3) and GCINT3-BR3 (SEQ ID NO:4). Adapter oligonucleotide include GC3A-R1 (SEQ ID NO:5), IACAdpt9 (SEQ ID NO:6), GC3A-R2 (SEQ ID NO:20), and ICAdpt10 (SEQ ID NO:21). Detection probes include CTGCUnv3 (SEQ ID NO:7), ICUnv4 (SEQ ID NO:8), MPC-DR (SEQ ID NO:22), and MPC2-FD (SEQ ID NO:23). IAC includes GCI3-IAC4 (SEQ ID NO:9).

SDA Assays with Dry Components and Linear Detection Probes

The components of the SDA assays in accordance with the present invention were optimized to a format where each component could be dried and rehydrated when needed. The concentrations of oligonucleotides and reagents for a 100 µl SDA reaction are listed below.

Oligonucleotides Utilized and Their Concentrations:
50 nM of bumper GCINT3-BL2
50 nM of bumper GCINT3-BR3
500 nM of amplification primer GCINT3-APL2
200 nM of amplification primer GCINT3-APR1
130 nM of adapter GC3A-R2
200 nM of adapter ICAdpt10
300 nM of detector MPC-FD
300 nM of detector MPC2-DR
300 copies of GCI3-IAC4

Concentrations of Reagent and Other Components:

60 mM potassium phosphate, (made from pH7.6 stock)

10% DMSO

9% glycerol 0.1 mM dATP, 0.1 mM dGTP, 0.1 mM dTTP, and 0.125 mM S isomer of α thioated dCTP 3.5 mM magnesium acetate 100 ug/ml BSA 1.84% trehalose 320 mM DTT 48 BD units BsoB1 restriction enzyme 8.4 BD units Bst polymerase This optimized reaction mix utilized GC3A-R2 (SEQ ID NO:20) and ICAdpt10 (SEQ ID NO:21) as adapter oligonucleotides, and MPC-DR (SEQ ID NO:22) and MPC2-FD (SEQ ID NO:23) as detection probes. The *Neisseria gonorrhoeae* target DNA amplification products were detected by MPC2-FD, which was labeled with fluorescein and dabcyl. The IAC (GCI3-IAC4) DNA amplification products were detected by MPC-DR, which was labeled with rhodamine and dabcyl. The detection probes MPC-DR and MPC2-FD do not need intramolecular hybridization (e.g., folding into a hairpin structure) to achieve quenching of the fluorescent dyes, since the dye and the quencher molecule are positioned in close proximity. A BsoB1 restriction site is present between the dye and the quencher molecule. Amplification of the *Neisseria gonorrhoeae* target DNA or the IAC leads to the generation of a second oligonucleotide complementary to the adapter oligonucleotide. The second oligonucleotide, which is complementary to the detection probe, anneals to the detection probe and generates a double strand DNA. The BsoB1 restriction enzyme recognizes the double stranded BsoB1 site between the dye and the quencher molecule and cleaves the site, which separates the fluorescent dye from the quenching molecule and generates the signal to be detected.

Example 3

Assay Sensitivity

The optimized reaction conditions described in Example 2 (see paragraph 064) were used to determine the sensitivity of a diplex SDA assay in accordance with the present invention. A strain of *Neisseria gonorrhoeae* (ATCC# 19424) was titrated from 1×10⁴ to 25 particles per SDA reaction. The *Neisseria gonorrhoeae* cells were lysed in a BD lyse block, added to the SDA reaction mixture, and then amplified in the BDProbeTec™ ET instrument. One hundred percent of the diplex SDA reactions containing *Neisseria gonorrhoeae* were positive, with detection values significantly greater than those seen for the negative control, and thus confirming that the diplex SDA assay of the invention is sensitive for *Neisseria gonorrhoeae* nucleic acid.

TABLE 4

*Neisseria gonorrhoeae* Limit of Detection Experiment

| | Cells/reaction: | | | | | | |
|---|---|---|---|---|---|---|---|
| | 10,000 | 1,000 | 500 | 100 | 50 | 25 | 0 |
| MOTA: | 76,990 | 97,390 | 92,160 | 86,960 | 82,290 | 78,980 | 450 |
| | 91,020 | 79,160 | 86,800 | 94,700 | 80,190 | 77,990 | 300 |
| | 17,910 | 98,710 | 99,150 | 86,920 | 94,000 | 69,940 | 710 |
| | 88,880 | 101,920 | 94,960 | 94,190 | 86,820 | 71,050 | 60 |
| | 10,1790 | 103,940 | 98,000 | 92,490 | 94,040 | 66,150 | 810 |
| | 85,750 | 100,460 | 88,840 | 92,880 | 94,730 | 72,240 | 40 |
| | 106,660 | 100,550 | 84,360 | 85,880 | 86,200 | 90,580 | 360 |
| | 99,990 | 99,990 | 91,600 | 90,360 | 78,380 | 79,340 | 140 |
| Mean: | 96124 | 97754 | 91984 | 90548 | 87956 | 75784 | 359 |

The optimized dry/rehydration reaction condition described in Example 2 (see paragraph 067) was also tested for its sensitivity. Different samples, which contained *Neisseria gonorrhoeae* cells (strain 19424) with different concentrations in 2 mls of buffer [30 mM potassium phosphate buffer (made from pH7.6 stock), 10% DMSO, and 9% glycerol], were lysed for 10 minutes at 114° C. in a BD Lyse Block. Samples were cooled for 15 minutes and 150 μl of each sample was transferred to the priming wells. The rehydrated samples in the priming wells were incubated for 20 minutes at room temperature followed by 10 minutes on a heat block set at 72.5° C. For each sample, 100 μl of the priming reaction mix was transferred to an amplification microwell previously heated for 10 minutes on a 54° C. heat block, followed by mixing 50 μl of the transferred volume three times in the amplification well. The plates were sealed and transferred into the BDProbeTec™ ET instrumented for 60 minutes at 52° C. Specimens having a reading of at least 4,000 MOTA (as determined by a Method Other Than Acceleration) were recorded as positive for *Neisseria gonorrhoeae* (i.e., the 4,000 MOTA reading was the cut-off value for a sample to be determined positive for *Neisseria gonorrhoeae*). MOTA is described in published European application no. 01110657.2, which is hereby incorporated by reference. The highest value that a sample negative for *Neisseria gonorrhoeae* target DNA achieved was 780 MOTA. The MOTA readings were obtained according to the BDProbeTec™ ET (Becton Dickinson, MD) manufacturer's instructions.

The data in Table 5 indicates that the diplex SDA assay according to the present invention can detect at least 5 *Neisseria gonorrhoeae* particles per reaction, in which the 95% LOD would be 8 copies per reaction.

TABLE 5

Analytical Sensitivity of Diplex SDA Assay for *Neisseria gonorrhoeae* with Optimized Drydown Reaction Mix

| | GC particles/reaction: | | | | | | | | | | | |
|---|---|---|---|---|---|---|---|---|---|---|---|---|
| | 100 | | 50 | | 25 | | 10 | | 5 | | 0 | |
| Assay: | GC | IAC | GC | IAC | GC | IAC | GC | IAC | GC | IAC | GC | IAC |
| MOTA Signal: | 35310 | 53810 | 29590 | 13020 | 29030 | 62760 | 17430 | 33260 | 1450 | 51720 | 70 | 23970 |
| | 40430 | 43470 | 37330 | 22980 | 29370 | 60730 | 21520 | 45650 | 7440 | 67860 | 50 | 28710 |
| | 44710 | 47850 | 30740 | 34010 | 38490 | 62380 | 21350 | 52550 | 30400 | 44520 | 0 | 27810 |
| | 42830 | 48900 | 41850 | 40070 | 26130 | 68260 | 20370 | 59350 | 16780 | 61070 | 0 | 33420 |
| | 45890 | 56330 | 33720 | 21230 | 37780 | 64060 | 24750 | 61590 | 10200 | 62770 | 0 | 31800 |
| | 46440 | 45940 | 32840 | 37910 | 11310 | 63130 | 9690 | 61080 | 9400 | 55130 | 0 | 21200 |
| | 41760 | 52050 | 27620 | 39700 | 44480 | 52060 | 6680 | 61080 | 9870 | 46970 | 0 | 24610 |
| | 45030 | 40540 | 28410 | 38390 | 26790 | 57070 | 4860 | 63420 | 37170 | 40580 | 40 | 25490 |
| | 47150 | 57830 | 25470 | 21300 | 27220 | 46500 | 20550 | 36150 | 21810 | 74400 | 10 | 30800 |
| | 52600 | 54100 | 25350 | 15400 | 28520 | 60980 | 13530 | 38000 | 8990 | 75350 | 0 | 36760 |
| | 46430 | 42930 | 26160 | 31500 | 13390 | 67020 | 4400 | 46070 | 11260 | 68370 | 20 | 33630 |
| | 37050 | 52130 | 20190 | 34580 | 13160 | 69200 | 22570 | 46970 | 800 | 69120 | 0 | 29870 |
| | 34160 | 52800 | 23670 | 25080 | 24550 | 46050 | 20930 | 30400 | 4250 | 69090 | 50 | 34660 |
| | 20010 | 27110 | 33000 | 17740 | 21280 | 61770 | 13980 | 44680 | 3780 | 57160 | 400 | 23850 |
| | 25030 | 25730 | 26260 | 37050 | 14160 | 54520 | 14990 | 43910 | 5640 | 48400 | 500 | 27940 |
| | 27650 | 43420 | 14870 | 43620 | 19400 | 49540 | 25170 | 37440 | 9280 | 39860 | 0 | 27460 |
| | 34430 | 16280 | 20170 | 11350 | 9410 | 60260 | 4980 | 37570 | 2190 | 50000 | 10 | 31130 |
| | 26700 | 23730 | 16510 | 23140 | 19250 | 56410 | 10520 | 44460 | 9130 | 52690 | 0 | 40930 |
| | 31450 | 29120 | 22860 | 15220 | 17710 | 56680 | 5650 | 46490 | 25800 | 40170 | 200 | 39490 |
| | 37310 | 35120 | 20210 | 27470 | 21120 | 53100 | 12180 | 51870 | 8220 | 50060 | 0 | 36480 |
| | 30480 | 40810 | 20400 | 17350 | 13670 | 60860 | 6640 | 50260 | 6070 | 43700 | 10 | 41690 |
| | | | 28530 | 18160 | 17810 | 44850 | 26520 | 42950 | 2050 | 59640 | 290 | 39220 |
| | | | 14210 | 31980 | 16390 | 47370 | 20220 | 41150 | 20010 | 14720 | 780 | 45520 |
| | | | 21600 | 18020 | 16010 | 35580 | 24280 | 33250 | 12640 | 43040 | | |
| Average: | 37,755 | 42,381 | 25,898 | 26,511 | 22,351 | 56,714 | 15,573 | 46,233 | 11,443 | 53,600 | 106 | 32,019 |

Example 4

Assay of *Neisseria gonorrhoeae* and Non *Neisseria gonorrhoeae* Species Specificity The specificity of the diplex SDA assay of the invention was determined using the oligonucleotides in Table 2 and the SDA reaction conditions described in Example 2: SDA Assays with Dry Components and Linear Detection Probes.

A panel of *Neisseria gonorrhoeae* strains was tested to determine the specificity of the diplex SDA assay of the invention. The assay detected one hundred percent of the *N. gonorrhoeae* strains when 250 cell particles per SDA reaction was tested (Table 6). A panel of *Neisseria* but non *gonorrhoeae* species and non *Neisseria* microorganisms were also tested in the diplex SDA assay of the invention (Table 7 and Table 8). The results in the tables are a summary of multiple experiments that addressed crossreactivity. The organisms were grown to one McFarland which, after processing, yielded approximately $1 \times 10^7$ cells/SDA reaction. The organisms listed in Table 7 and 8 were tested at that concentration, with the exception being *C. trachomatis* at $1 \times 10^6$ EBs/reaction. The IAC result allowed for the determination that a negative test result was due to a lack of crossreactivity with the assay's oligonucleotides, and not due to an inhibitor of amplification present in a processed sample. One strain of *N. cinerea* (#565) (previously identified as *N. lactamica*) led to the Diplex GC assay's IAC not being detected. The IAC was detected in the assay post a dilution of the sample ($1 \times 10^5$ cells/SDA reaction). This diluted sample also produced a Negative result for crossreactivity. Two strains of *Neisseria lactamica* (#23970 and 391) were determined to crossreact with the assay. Additionally, a very weak positive result was detected with 1 out of 3 replicates of *Branhamella catarrhalis* strain #25240. All strains of *Neisseria kochii* were positive with the SDA assay for *Neisseria gonorrhoeae*. This was expected since the organism has been identified as a subspecies of *Neisseria gonorrhoeae*.

These results demonstrate the crossreactivity pattern of the assay described in this invention.

TABLE 6

*Neisseria gonorrhoeae* strains

| Organism | Strain | Source | Result |
|---|---|---|---|
| Neisseria gonorrhoeae | 19424 | ATCC | Pos. |
| Neisseria gonorrhoeae | 35542 | ATCC | Pos. |
| Neisseria gonorrhoeae | 43069 | ATCC | Pos. |
| Neisseria gonorrhoeae | 43070 | ATCC | Pos. |
| Neisseria gonorrhoeae | 49226 | ATCC | Pos. |
| Neisseria gonorrhoeae | 51109 | ATCC | Pos. |
| Neisseria gonorrhoeae | 454 | BD | Pos. |
| Neisseria gonorrhoeae | 1632 | BD | Pos. |
| Neisseria gonorrhoeae | 2900 | BD | Pos. |
| Neisseria gonorrhoeae | 111 | CDC | Pos. |
| Neisseria gonorrhoeae | 4 | BD | Pos. |
| Neisseria gonorrhoeae | 20 | BD | Pos. |
| Neisseria gonorrhoeae | 98 | BD | Pos. |
| Neisseria gonorrhoeae | 115 | BD | Pos. |
| Neisseria gonorrhoeae | 497 | BD | Pos. |
| Neisseria gonorrhoeae | 1588 | BD | Pos. |
| Neisseria gonorrhoeae | 1618 | BD | Pos. |
| Neisseria gonorrhoeae | 2373 | BD | Pos. |
| Neisseria gonorrhoeae | 3981 | BD | Pos. |
| Neisseria gonorrhoeae | 8000 | BD | Pos. |
| Neisseria gonorrhoeae | 8002 | BD | Pos. |
| Cloned *Neisseria gonorrhoeae* DNA (plasmid) | N/A | N/A | Pos. |
| Negative Control | N/A | N/A | Neg. |

TABLE 7

Neisseria Species Crossreactants

| Organism | Strain/Organism # | Site | Result |
|---|---|---|---|
| Neisseria cinerea | 232 | BD | Neg. |
| Neisseria cinerea | 565 | BD | Neg. |
| Neisseria elongata | 25295 | ATCC | Neg. |
| Neisseria elongata ss nitroreduscens | 49377 | BD | Neg. |
| Neisseria elongate ss nitroreduscens | 49378 | ATCC | Neg. |
| Neisseria elongata ss glycolytica | 29315 | ATCC | Neg. |
| Neisseria flava | nrl 30008 | HVMC | Neg. |
| Neisseria flava | nrl 30034 | HVMC | Neg. |
| Neisseria flava | nrl 30037 | HVMC | Neg. |
| Neisseria flava | nrl 30136 | HVMC | Neg. |
| Neisseria flava | nrl 30137 | HVMC | Neg. |
| Neisseria flavescens | 13120 | ATCC | Neg. |
| Neisseria flavescens | 13115 | ATCC | Neg. |
| Neisseria flavescens | 13116 | ATCC | Neg. |
| Neisseria flavescens | 13117 | ATCC | Neg. |
| Neisseria lactamica | 264 | BD | Neg. |
| Neisseria lactamica | 391 | BD | Pos. |
| Neisseria lactamica | 408 | BD | Neg. |
| Neisseria lactamica | 803 | BD | Neg. |
| Neisseria lactamica | 23970 | ATCC | Pos. |
| Neisseria lactamica | 7624 | BD | Neg. |
| Neisseria lactamica | 216-75 | ATCC | Neg. |
| Neisseria meningitidis | 13077 | ATCC | Neg. |
| Neisseria meningitidis | 305 | BD | Neg. |
| Neisseria meningitidis | 14685 | ATCC | Neg. |
| Neisseria meningitidis | 35699 | BD | Neg. |
| Neisseria meningitidis | 41799 | BD | Neg. |
| Neisseria meningitidis | 55592 | ATCC | Neg. |
| Neisseria meningitidis | 1490 | CCF | Neg. |
| Neisseria meningitidis | 2039 | CCF | Neg. |
| Neisseria meningitidis | 2040 | CCF | Neg. |
| Neisseria meningitidis | c136 | CCF | Neg. |
| Neisseria meningitidis(768) | 301 | BD | Neg. |
| Neisseria meningitidis (LRD728) | 53900 | BD | Neg. |
| Neisseria muscosa | 19693 | ATCC | Neg. |
| Neisseria muscosa | 19694 | ATCC | Neg. |
| Neisseria muscosa | 19695 | ATCC | Neg. |
| Neisseria mucosa | 19696 | ATCC | Neg. |
| Neisseria muscosa | 1915 | CCF | Neg. |
| Neisseria perflava | 6573 | BD | Neg. |
| Neisseria perflava | 8078 | BD | Neg. |
| Neisseria perflava | 8028 | BD | Neg. |
| Neisseria perflava | nrl 30015 | HVMC | Neg. |
| Neisseria perflava | nrl 30035 | HVMC | Neg. |
| Neisseria perflava | nrl 35304 | HVMC | Neg. |
| Neisseria perflava | nrl 35308 | HVMC | Neg. |
| Neisseria perflava | nrl 35320 | HVMC | Neg. |
| Neisseria polysaccharea | 1574 | CCF | Neg. |
| Neisseria polysaccharea | 43768 | ATCC | Neg. |
| Neisseria sicca | Msdh | BD | Neg. |
| Neisseria sicca | 29256 | ATCC | Neg. |
| Neisseria sicca | 29259 | ATCC | Neg. |
| Neisseria sicca | 891 | CCF | Neg. |
| Neisseria sicca | 9913 | ATCC | Neg. |
| Neisseria subflava | 10555 | BD | Neg. |
| Neisseria subflava | 7697 | BD | Neg. |
| Neisseria subflava | 7858 | BD | Neg. |
| Neisseria subflava | 209 | CCF | Neg. |
| Neisseria subflava | 616 | CCF | Neg. |
| Neisseria subflava | 1253 | CCF | Neg. |
| Neisseria subflava | 1378 | CCF | Neg. |
| Neisseria subflava | 1889 | CCF | Neg. |
| Neisseria subflava | 2007 | CCF | Neg. |
| Neisseria subflava | nh14 | Farrell | Neg. |
| Neisseria subflava | nh15 | Farrell | Neg. |
| Neisseria subflava | nh18 | Farrell | Neg. |
| Neisseria subflava | nh7 | Farrell | Neg. |
| Neisseria subflava | nh8 | Farrell | Neg. |
| Neisseria subflava | nh9 | Farrell | Neg. |
| Neisseria weaveri | 1246 | CCF | Neg. |
| Neisseria weaveri | 1399 | CCF | Neg. |
| Neisseria weaveri | 1862 | CCF | Neg. |
| Neisseria kochii | 31291 | NRL | Pos. |
| Neisseria kochii | 31292 | NRL | Pos. |
| Neisseria kochii | 31294 | NRL | Pos. |
| Neisseria kochii | 32895 | NRL | Pos. |
| Neisseria kochii | 32896 | NRL | Pos. |
| Negative Control | N/A | N/A | Neg. |

TABLE 8

Non Neisseria Crossreactants

| Non Neisseria Crossreactants | ATCC or ID. | Source | Result |
|---|---|---|---|
| Acinetobacter calcoaceticus | 13339 | ATCC | Neg. |
| Acinetobacter lwolfi | 19001 | ATCC | Neg. |
| Actinomyces israelii | 10049 | ATCC | Neg. |
| Aeromonas hydrophila | 7966 | ATCC | Neg. |
| Alcaligenes faecalis | 8750 | ATCC | Neg. |
| Bacillus subtilis | 12100 | ATCC | Neg. |
| Bacteroides fragilis | 25285 | ATCC | Neg. |
| Branhamella catarrhalis | 25238 | ATCC | Neg. |
| Branhamella catarrhalis | 25240 | ATCC | *Weak Pos. |
| Branhamella catarrhalis | 25238 | ATCC | Neg. |
| Branhamella catarrhalis | c223 | CCF | Neg. |
| Branhamella catarrhalis | c224 | CCF | Neg. |
| Branhamella catarrhalis | c225 | CCF | Neg. |
| Candida albicans | 44808 | ATCC | Neg. |
| Candida glabrata | 2001 | ATCC | Neg. |
| Candida tropicalis | 750 | ATCC | Neg. |
| Chlamydia pneumoniae | AR-39 | ATCC | Neg. |
| Chlamydia psittaci | Cal-10 | BD | Neg. |
| Chlamydia trachomatis | LGV II | BD | Neg. |
| Citrobacter freundii | 8090 | ATCC | Neg. |
| Clostridium perfringens | 13124 | ATCC | Neg. |
| Corynebacterium renale | 19412 | ATCC | Neg. |
| Cryptococcus neoformans | 36556 | ATCC | Neg. |
| Edwardsiella tarda | 15469 | ATCC | Neg. |
| Enterobacter cloacae | 13047 | ATCC | Neg. |
| Enterococcus faecalis | 29212 | ATCC | Neg. |
| Enterococcus faecium | 19434 | ATCC | Neg. |
| Escherichia coli | 11775 | ATCC | Neg. |
| Flavobacterium meningosepticum | 13253 | ATCC | Neg. |
| Gardnerella vaginalis | 14018 | ATCC | Neg. |
| Gemella haemolysans | 10379 | ATCC | Neg. |
| Haemophilus influenzae | 33533 | ATCC | Neg. |
| Kingella kingae | 23330 | ATCC | Neg. |
| Klebsiella pneumoniae | 13883 | ATCC | Neg. |
| Lactobacillus acidophilus | 4356 | ATCC | Neg. |
| Lactobacillus brevis | 14869 | ATCC | Neg. |
| Lactobacillus jensenii | 25258 | ATCC | Neg. |
| Listeria monocytogenes | 7644 | ATCC | Neg. |
| Moraxella lacunata | 17967 | ATCC | Neg. |
| Moraxella osloensis | 9281 | BD | Neg. |
| Morganella morganii | 25830 | ATCC | Neg. |
| Peptostreptococcus anaerobius | 27337 | ATCC | Neg. |
| Peptostreptococcus asaccharolyticus | 29743 | ATCC | Neg. |
| Peptostreptococcus productus | 27340 | ATCC | Neg. |
| Plesiomonas shigelloides | 14029 | ATCC | Neg. |
| Propionibacterium acnes | 6919 | ATCC | Neg. |
| Providencia stuartii | 35031 | ATCC | Neg. |
| Pseudomonas aeruginosa | 27853 | ATCC | Neg. |
| Salmonella minnesota | 9700 | ATCC | Neg. |
| Salmonella typhimurium | 13311 | ATCC | Neg. |
| Staphylococcus aureus | 25923 | ATCC | Neg. |
| Staphylococcus epidermidis | E155 | ATCC | Neg. |
| Streptococcus agalactiae | 12386 | ATCC | Neg. |
| Streptococcus mitis | 9811 | ATTC | Neg. |
| Streptococcus mutans | 25175 | ATCC | Neg. |
| Streptococcus pneumoniae | 6303 | ATCC | Neg. |

TABLE 8-continued

Non *Neisseria* Crossreactants

| Non *Neisseria* Crossreactants | ATCC or ID. | Source | Result |
|---|---|---|---|
| *Streptococcus pyogenes* | 19615 | ATCC | Neg. |
| *Streptomyces griseus* | 10137 | ATCC | Neg. |
| *Veillonella parvula* | 10790 | ATCC | Neg. |
| *Vibrio parahaemolyticus* | 17802 | ATCC | Neg. |
| *Yersinia enterocolitica* | 27729 | ATCC | Neg. |

Example 5

Demonstration of Diplex SDA Assay for *Neisseria gonorrhoeae*

The following data demonstrates the ability of a diplex SDA assay for *Neisseria gonorrhoeae* to amplify and detect two target DNA sources (*Neisseria gonorrhoeae* target DNA and an IAC, e.g., GCI3-IAC4 (SEQ ID NO:9)). This experiment utilized the primary oligonucleotides in Table 2 and the SDA reaction conditions described in Example 2 (see paragraph 067). The data listed in Table 9 demonstrates that the diplex SDA assay for *Neisseria gonorrhoeae* can amplify and detect, in a single assay well, both *Neisseria gonorrhoeae* DNA (GC) and the internal amplification control (IAC). The two DNA target sources were distinguished by the use of different fluorescently labeled detection probes: rhodamine (ROX) for *Neisseria gonorrhoeae* and fluorescein (FAM) for the IAC. The *Neisseria gonorrhoeae* DNA and the IAC can be amplified and detected when they were present alone (Conditions 1 & 2), indicating the ability of the assay to detect both target DNA and the IAC. The *Neisseria gonorrhoeae* target sequence was also detected in the presence of the IAC (Condition 3). The *Neisseria gonorrhoeae* signal was not significantly altered when IAC was present. The IAC signal was found to be suppressed in Condition 3. However, this does not reflect on the specificity or sensitivity of the assay, as it is important for the IAC to be detected in the absence of *Neisseria gonorrhoeae* to indicate a lack of inhibitors or presence of human error.

TABLE 9

Dual Detection Experiment

| | Condition # 1 | | Condition # 2 | | Condition # 3 | |
|---|---|---|---|---|---|---|
| | ROX | FAM | ROX | FAM | ROX | FAM |
| GC Target | 100 | 100 | 0 | 0 | 100 | 100 |
| IAC Target | 0 | 0 | 300 | 300 | 300 | 300 |
| MOTA: | 68060 | 1220 | 240 | 39900 | 71370 | 11440 |
| | 52860 | 2580 | 40 | 50650 | 57370 | 14430 |
| | 81610 | 1760 | 160 | 51570 | 67760 | 18230 |
| | 53710 | 1400 | 170 | 69930 | 89480 | 7720 |
| | 82700 | 2410 | 150 | 60770 | 75250 | 8210 |
| | 55320 | 3000 | 30 | 75640 | 85300 | 12380 |
| Mean: | 65710 | 2062 | 132 | 58077 | 74422 | 12068 |

REFERENCE CITED AND EQUIVALENTS

All references cited herein are incorporated herein by reference in their entirety and for purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for detecting a *Neisseria gonorrhoeae* target sequence comprising:
   (a) amplifying the target sequence using a first amplification primer having a sequence comprising the target binding sequence of SEQ ID NO:1 or SEQ ID NO:2 and;
   (b) detecting the amplified target sequence.

2. The method of claim 1 further comprising a second amplification primer have a sequence comprising the target binding sequence of any one of SEQ ID NOS: 1–6, 10–18, or 20–21.

3. The method of claim 1 wherein:
   (a) the first amplification primer comprises the target binding sequence of SEQ ID NO:1; and
   (b) the second amplification primer comprises the target binding sequence of SEQ ID NO:2.

4. The method of claim 1 wherein said amplification reaction is a Strand Displacement Amplification (SDA) reaction.

5. The method of claim 1 wherein said amplification or detection reaction is selected from the group consisting of direct detection, polymerase chain reaction (PCR), in situ hybridization, transcription mediated amplification (TMA), self sustained sequence replication (SSR) rolling circle amplification or nucleic acid sequence based amplification (NASBA).

6. The method of claim 2 wherein the second amplification primer is selected such that the 3' end of the target binding sequence of the second oligonucleotide overlaps the 5' end of the target binding sequence of the first oligonucleotide.

7. The method of claim 1 wherein the first amplification primer further comprises a hairpin, G-quartet, restriction site or a sequence which hybridizes to a reporter probe.

8. The method of claim 1 wherein the first amplification primer further comprises a detectable label.

9. The method of claim 8 wherein the label is a fluorescent label.

10. The method of claim 1 wherein the first amplification primer further comprises a restriction endonuclease recognition site or a RNA polymerase promoter.

11. The method of claim 1 further comprising amplifying an internal amplification control (IAC).

12. The method of claim 11 wherein the IAC comprises SEQ ID NO:9 or SEQ ID NO:19.

13. The method of claim 11 further comprising detection of amplified IAC.

14. The method of claim 13 wherein the amplified IAC is detected by a means different from the amplified target sequence.

15. A method for detecting a *Neisseria gonorrhoeae* target sequence comprising:
   (a) hybridizing one or more amplification primers having a sequence comprising the target binding sequence of SEQ ID NO:1 or SEQ ID NO:2 and;
   (b) detecting said hybridized amplification primer.

16. The method of claim 15 wherein said one or more amplification primers further comprises a detectable label.

17. The method of claim 15 wherein said detectable label is fluorescent.

* * * * *